(12) United States Patent
Mata

(10) Patent No.: US 11,202,765 B2
(45) Date of Patent: Dec. 21, 2021

(54) MULTIFUNCTIONAL TOPICAL CREAM COMPRISING BETA-CARYOPHYLLENE, ESSENTIAL OILS, IN A PHOSPHOLIPID AND TRIGLYCERIDE BASE

(71) Applicant: John Enrique Mata, Corvallis, OR (US)

(72) Inventor: John Enrique Mata, Corvallis, OR (US)

(73) Assignee: John Enrique Mata, Corvallis, OR (US)

( * ) Notice: Subject to any disclaimer, the term of this patent is extended or adjusted under 35 U.S.C. 154(b) by 0 days.

(21) Appl. No.: 16/039,230

(22) Filed: Jul. 18, 2018

(65) Prior Publication Data

US 2020/0030252 A1    Jan. 30, 2020

(51) Int. Cl.
| | | |
|---|---|---|
| *A61K 31/015* | (2006.01) | |
| *A61K 9/00* | (2006.01) | |
| *A61K 9/06* | (2006.01) | |
| *A61K 47/14* | (2017.01) | |
| *A61K 47/24* | (2006.01) | |
| *A61K 47/44* | (2017.01) | |

(52) U.S. Cl.
CPC .......... *A61K 31/015* (2013.01); *A61K 9/0014* (2013.01); *A61K 9/06* (2013.01); *A61K 47/14* (2013.01); *A61K 47/24* (2013.01); *A61K 47/44* (2013.01)

(58) Field of Classification Search
None
See application file for complete search history.

(56) References Cited

U.S. PATENT DOCUMENTS

2011/0008465 A1 *   1/2011   Legault ................ A61K 31/337
                                                          424/649
2018/0042890 A1 *   2/2018   Sinai ...................... A61K 31/05

FOREIGN PATENT DOCUMENTS

WO         WO-2015000064 A1 *   1/2015  ............. A61K 36/67

OTHER PUBLICATIONS

A web-page obtained from the Wikipedia website https://en.wikipedia.org/wiki/Caryophyllene (date unknown).*
"Plantasens Olive Active HP, Anti-Aging Active" a technical datasheet supplied by Clariant (dated Jul. 7, 2015) (Year: 2015).*

* cited by examiner

*Primary Examiner* — Sin J Lee
(74) *Attorney, Agent, or Firm* — Randolph Bretton; The Law Office of Randolph Bretton

(57) ABSTRACT

A novel pharmaceutical composition is provided comprising beta-caryophyllene or a functionally equivalent derivative, analogue or pharmaceutically acceptable salt thereof in a base cream comprising triglycerides, phospholipid, water, wax, alcohol, with other minor constituents. The composition is useful to treat pain and/or inflammation, reduce fine lines and wrinkles, moisturize, and protect skin with anti-bacterial, anti-fungal and insect repelling properties.

4 Claims, No Drawings

MULTIFUNCTIONAL TOPICAL CREAM COMPRISING BETA-CARYOPHYLLENE, ESSENTIAL OILS, IN A PHOSPHOLIPID AND TRIGLYCERIDE BASE

CROSS REFERENCE TO RELATED APPLICATIONS

Not Applicable

STATEMENT REGARDING FEDERALLY SPONSORED RESEARCH OR DEVELOPMENT

Not Applicable

REFERENCE TO SEQUENCE LISTING, A TABLE, OR A COMPUTER PROGRAM LISTING COMPACT DISK APPENDIX

Not Applicable

FIELD OF THE INVENTION

The present invention generally relates to the treatment and protection of mammalian skin for pain and/or inflammation relief, aging, colonization by bacteria or fungi and prevention of insect bites and in particular, relates to a composition useful to treat multiple conditions mentioned herein.

BACKGROUND OF THE INVENTION

Perception of pain is a condition that demonstrates high inter-individual variability affected, in part, by age, gender, race, ethnicity, mood states, stress and previous experiences with treatments. The presentation of pain includes, but is not limited to, inflammatory, neuropathic and cancer related. Given that pain is a symptom of underlying condition(s) the use of multi-targeting strategies in addressing pain is common.

Multi-component therapy, in which two or more agents interact simultaneously to address a condition is a rational and efficacious form of therapy. One of the advantages of multi-component therapy is the potential synergistic effect of the combination, e.g. an effect which is greater than the sum of the expected individual effects. In addition to the use of multicomponent therapy for a single condition such as pain, two or more agents may also constitute a formulation to address multiple conditions. Careful formulations therefore can address a multitude of conditions resulting in optimum health through relief of symptoms of pain, inflammation, aging, and reduced susceptibility to contact from pathogens and insects. While therapeutic modalities exist to address these individual conditions the use of multi-target multi-component therapy may result in reduced side-effects, reduced toxicity, and improved compliance over single target therapies.

It would be desirable to develop a multi-component therapeutic for the treatment and prophylaxis of a multitude of conditions that could include, but not limited to, symptoms of pain, inflammation, aging, and reduced susceptibility to contact from pathogens and insects.

SUMMARY OF THE INVENTION

A novel composition has now been developed for a multitude of conditions that could include, but not limited to, symptoms of pain, inflammation, aging, and reduced susceptibility to contact from pathogens and insects.

Accordingly, in one aspect of the invention, a composition is provided comprising beta-caryophyllene or a functionally equivalent derivative, analogue or pharmaceutically acceptable salt thereof, in a suitable adjuvant containing phospholipids and triglycerides.

In another aspect of the invention, a method of treating pain and/or inflammation in a mammal is provided comprising administering to the mammal a composition comprising beta-caryophyllene or a functionally equivalent derivative, analogue or pharmaceutically acceptable salt thereof, and a suitable adjuvant.

In another aspect, an article of manufacture is provided comprising packaging and a composition, wherein the composition comprises beta-caryophyllene or a functionally equivalent derivative, analogue or pharmaceutically acceptable salt thereof, and the packaging indicates that the composition is useful to treat pain and/or inflammation.

These and other aspects of the invention will become apparent in the following detailed description and examples.

DETAILED DESCRIPTION OF THE INVENTION

A composition for the treatment and prophylaxis of a multitude of conditions that could include, but not limited to, symptoms of pain, inflammation, aging, and reduced susceptibility to contact from pathogens and insects comprising beta-caryophyllene or a functionally equivalent derivative, analogue or pharmaceutically acceptable salt thereof, and an adjuvant containing a combination of phospholipids and triglycerides or functionally equivalent derivatives, analogue or pharmaceutically acceptable salt thereof.

The term "beta-caryophyllene" is used herein to encompass the secondary metabolite, bicyclic sesquiterpene,-4,11,11-trimethyl-8-methylene-bicyclo[7.2.0]undec-4-ene, which is present in, for example, plant-derived oleoresins, essential oils, solutes, distillates, extracts, fermentations, infusions and leaching, from plants including, but not limited to, *Cannabis* spp. including *Cannabis sativa*, *Cannabis indica* and *Cannabis ruderalis*, *Humulus lupulus*, *Carum nigrum*, *Eugenia caryophyllata*, *Ocimum micranthum*, *Origanum vulgare*, *Piper guineense*, *Cinnamomum zeylanicum*, *Carthamus tinctorius*, *Helichrysum italicum*, *Copaifera* spp. including *Copaiba officinalis*, *Copaibaguianensis*, *Copaiba martii hayne*, *Copaiba duckei*, *Copaiba reticulata*, *Copaiba multijuga*, *Copaiba confertiflora*, *Copaiba langsdorffii*, *Copaiba coriacea*, *Copaiba trapezifolia*, *Copaiba lucens*, *Copaiba paupera* and *Copaiba cearensis*, *Syzygium aromaticum* (clove), *Piper nigrum* (black pepper), *Zingiber nimmoni*, *Zingiber officinale*, *Ocimum canum*, *Ocimum selloi*, *Piper cubeba*, *Aframomum melegueta*, *Panax ginseng*, *Zanthoxylum piperitum*, *Zanthoxylum simulans*, *Zanthoxylum bungeanum*, *Zanthoxylum rhesta*, *Zanthoxylum acanthopodium*, *Zanthoxylum piperitum*, *Syzgium aromaticum*, *Mentha longifolia*, *Ocimum tenuiflorum*, *Micromeria fruticosa*, *Salvia triloba*, *Salvia canariensis*, *Rosmarinus officinalis*, *Satureja thymbra*, *Satureja montana*, *Micromeria fruticosa* subsp. *Barbata*, *Piper longum*, *Piper retrofractum*, *Satureja obovata*, *Schinus terebinthifolius*, *Spilanthes acmella*, *Spilanthes oleracea*, *Persicaria hydropiper*, *Artemisia abrotanum*, *Persicaria odorata*, *Rhus coriaria*, *Xylopia aethiopica*, *Cymbopogon citratis*, *Pandanus amaryllifolius*, *Myrica gale*, *Myrica cerifera*, *Myrica pensylvanica*, *Origanum heracleoticum*, *Ocimum kilimandscharicum*, *Melissa officinalis*, *Mentha acquatica*, *Salvia* officinalis, *Salvia gillesii*, *Hyssopus officinalis*, *Thymus vulgaris*, *Teucrium cyprium*, *Teucrium divaricatum* var. *canescens*, *Artemisia salsoloides*, *Thymus zygis* subsp. *Sylvestris*, *Teucrium chamaedrys*, *Origanum minutiflorum*, *Ocimum basilicum*, *Thymus* x *citriodorus*, *Micromeria Juliana*, *Origanum onites*, *Origanum vulgare* subsp. *hirtum*, *Rosmarinus tomentosus*, *Lippia alba*, *Thymus riatarum*, *Rosemarinus eriocalyx*, *Ageratum conyzoides*, *Teucrium arduini*, *Teucrium kotschyanum*, *Nepeta racemosa*, *Rosmariunus* x *lavandulaceus*, *Thymus funkii*, *Coridothymus capitatus*, *Origanum syriacum*, *Thymus cilicicus*, *Eucalyptus porosa*, *Laurus nobilis*, *Daucas carota*, *Eucalyptus leucoxylon*, *Teucrium micropodioides*, *Leonotis leonurus*, *Micromeria varia* subsp. *thymoides*, *Hyptis suaveolens*, *Plectranthus coleoides*, *Vitex agnus-castus*, *Calamintha nepeta*, *Micromeria myrtifolia*, *Mentha aquatic*, *Salvia dorisiana*, *Ocimum suave*, *Sideritis scardica*, *Plectranthus incanus*, *Mentha* x *piperita*, *Hyssopus officinalis* subsp. *aristatus*, *Rosmarinus* x *mendizabalii*, *Satureja subspicata* subsp. *librnica*, *Sideritis mugronesis*, *Eucalyoptus fasiculosa*, *Teucrium gnaphalodes*, *Dictamnus albus*, *Satureja cilicica*, *Monardia citriodora*, *Sideritis germanicolpitana*, *Zingiber officinale*, *Eucalyptus sparsa*, *Thymus longicaulis*, *Origanum vulgare* var. *gracile*, *Minthostachys mollis*, *Monardia didyma*, *Salvia sclarea*, *Eucalyptus melanophloia*, *Elsholtzia blanda*, *Eucalyptus desquamate*, *Teucrium pseudoscorodonia*, *Eucalyptus cuprea*, *Sideritis pauli*, *Eucalyptus lansdowneana*, *Teucrium salviastrum*, *Teucrium scorodonia*, *Elsholtzia eriostachya* var. *pusilla*, *Sideritis athoa*, *Aralia cordata*, *Eucalyptus intertexta*, *Teurcrium oxylepis* subsp. *oxylepis*, *Cleaonia lusitanica*, *Satureja cuneifolia*, *Eucalyptus largisparsa*, *Eucalyptus odorata*, *Teurcrium polium* var. *valentinum*, *Eucalyptus behriana*, *Eucalyptus populnea*, *Teurcrium oxylepis* subsp. *marianum*, *Origanum vulgare* var. *viride*, *Eucalyptus ochrophloia*, *Eucalyptus viridis*, *Teucrium asiaticum*, *Thymus zygis*, *Lonicera japonica*, *Achillea millefolium*, *Aesculus hippocastanum*, *Agastache rugosa*, *Alpinia galangal*, *Anethum graveolens*, *Angelica archangelica*, *Annona squamosal*, *Apium graveolens*, *Artemisia absinithium*, *Artemisia annua*, *Artemisia capillaris*, *Bidens pilosa*, *Boswellia sacra*, *Camellia sinensis*, *Carum carvi*, *Centella asiatica*, *Chamaemelum nobile*, *Chrysanthemum parthenium*, *Chrysanthemum* x *morifolium*, *Cinnamomum aromaticum*, *Cinnamomum camphora*, *Cinnamomum verum*, *Citrus limon*, *Citrus paradise*, *Citrus reticulate*, *Citrus sinensis*, *Coleus barbatus*, *Coriandrum sativum*, *Croton eluteria*, *Croton lechleri*, *Ellettaria cardamomum*, *Ephedra sinica*, *Eruca sativa*, *Eucalyptus albens*, *Eucalyptus angulosa*, *Eucalyptus astringens*, *Eucalyptus blakelyi*, *Eucalyptus bosistoana*, *Eucalyptus botryoides*, *Eucalyptus brassiana*, *Eucalyptus camaldulensis*, *Eucalyptus ceratocorys*, *Eucalyptus cladocalyx*, *Eucalyptus dealbata*, *Eucalyptus diversicolor*, *Eucalyptus dolichorhyncha*, *Eucalyptus erythrandra*, *Eucalyptus forrestiana*, *Eucalyptus globulus*, *Eucalyptus grandis*, *Eucalyptus incrassate*, *Eucalyptus maculata*, *Eucalyptus maiden*, *Eucalyptus melliodora*, *Eucalyptus moluccana*, *Eucalyptus occidentalis*, *Eucalyptus oviformis*, *Eucalyptus polyanthemos*, *Eucalyptus puncata*, *Eucalyptus siderophloia*, *Eucalyptus sideroxylon*, *Eucalyptus stoatei*, *Eucalyptus tereticornis*, *Eucalyptus tetraptera*, *Foeniculum vulgare*, *Hedychium flavum*, *Houttuynia cordata*, *Lantana camara*, *Leptospermum scoparium*, *Lindera benzoin*, *Magnolia denudate*, *Matricaria recutita*, *Malaleuca altemifolia*, *Melia azedarach*, *Mentha arvensis* var. *piperascens*, *Mentha pulegium*, *Mentha rotundifolia*, *Mentha spicata*, *Montanoa tomentosa*, *Murraya koenigii*, *Myrciaria dubia*, *Myristica fragrans*, *Myrrhis odorata*, *Nepeta cataria*, *Ocimum gratissimum*, *Panax ginseng*, *Pelargonium citrosum*, *Perilla frutescens*, *Petroselinum crispum*, *Pimenta dioica*, *Pimenta racemosa*, *Pimpinella anisum*, *Pinus strobus*, *Piper nigrum*, *Pistacia lentiscus*, *Populus tacamahacca*, *Psidium guajava*, *Ptychopetalum olacoides*, *Ravensara aromatic*, *Sambucus nigra*, *Vaccinium myrtillus*, *Sassafras albidum*, *Satureja hortensis*, *Stevia rebaudiana*, *Illicium verum*, *Gossypium* sp., *Tagetes filifolia*, *Tagetes lucida*, *Tagetes minuta*, *Tamarindus indica*, *Tanacetum parthenium*, *Teucrium polium*, *Trifolium pretense*, *Valeriana officinalis*, *Zea mays*, *Piper betel*, *Pycnanthemum tenuifolium*, *Thymus serpyllum*, *Pycnanthemum setosum*, *Pycnanthemum pycnanthemoides*, *Pycnanthemum virginianum*, *Thymus orospedanus*, *Pycnanthemum clinopodioides*, *Pycnanthemum loomisii*, *Pilocarpus microphyllus*, *Hedeoma hispida*, *Lavandula* x *intermedia*, *Cymbopogon nardus*, *Pycnanthemum pilosum*, *Cuminum cyminum*, *Pycnanthemum verticillatum*, *Thymus capitatus*, *Pycnanthemum muticum*, *Lepechinia calycina*, *Aloysia citrodora*, *Dracocephalum thymiflora*, *Leonurus cardiac*, *Lepechinia schiediana*, *Scutellaria galericulata*, *Hedeoma pulegioides*, *Micromeria croatica*, *Pycnanthemum californicum*, *Cunila origanoides*, *Pycnanthemum torreyi*, *Thymus mastichina*, *Lycopus europeus*, *Moldavica thymiflora*, *Juniperis communis*, *Satureja vulgaris*, *Elsholtzia polystachya*, *Lycopus virginicus*, *Scutellaria churchilliana*, *Pycnanthemum montanum*, *Agastache foeniculum*, *Agastache nepetoides*, *Carthamus tinctorius*, *Dracocephalum parviflora*, *Pycnanthemum beadle*, *Scutellaria parvula*, *Echinacea* spp, *Galeopsis tetrahit*, *Satureja douglasii*, *Balotta nigra*, *Ribes nigrum*, *Isanthus brachiatus*, *Moldavica parviflora*, *Elsholtzia cristata*, *Elsholtzia pilosa*, *Myrtus communis*, *Cordia verbenacea*, *Ferula galbaniflua*, *Commiphora gileadensis*, *Populus balsamifera*, *Citrus bergamia*, *Tanacetum annum*, *Abies balsamea*, *Ocimum basilicum* ct *linalool*, *Mentha citrate*, *Picea mariana*, *Malaleuca leucadendron* var. *cajuputi*, *Eriocephalus punctulatus*, *Cymbopogon winterianus*, *Pinus nigra laricio*, *Cupressus sempervirens*, *Psudotsuga menzies*, *Canarium luzonicum*, *Eucalyptus citriodora*, *Eucalypotus dives*, *Eucalyptus radiata*, *Agonis fragrans*, *Bowsellia carterii*, *Pelargonium roseum* x *asperum*, *Helichrysum bracteiferum*, *Helichrysum gymnocephalum*, *Helichrysum odoratissimum*, *Tsuga Canadensis*, *Malaleuca teretifolia*, *Citrus hystrix*, *Kunzea ambigua*, *Larix laricina*, *Lavendula angustifolia*, *Lavendula officinalis*, *Cymbopogon citradis*, *Cymbopogon citratus* ct *rhodinol*, *Citrus aurantifolia*, *Bursera delpechiana*, *Origanum marjorana*, *Litsea cubeba*, *Citrus aurantium* var. *amara*, *Malaleuca quinquenervia* ct 1, 8 cineole, *Pinus resinosa*, *Cymbopogon martini* var. *motia*, *Pogostemom cablin*, *Citrus aurantium* var. *bigardia*, *Pinus edulis*, *Pinus ponderosa*, *Cinnamomum camphor* act 1, 8 cineole, *Rhododendron anthopogon*, *Rose damascena*, *Rosa damascena/Pelargonium Roseum* x *asperum*, *Rosmarinus officinalis* ct camphor, *Rosmarinus officinalis* ct verbenone, *Aniba rosaeodora*, *Cinnamosma fragrans*, *Pinus sylvestris*, *Abies sibirica*, *Abies alba*, *Lavandula latifolia*, *Hypericum perforatum*, *Cinnamomum glaucescens*, *Cinnamomum tamala*, *Thymus zygis*, *Thymus vulgaris* ct linalool, *Ocimum sanctum* ct eugenol, *Thymus vulgaris* ct thymol, *Curcuma longa*, *Picea glance*, *Zanthoxylum armatum*, *Cananga odorata*, *Ocimum mircanthum*, *Ocimum selloi*, *Citrus junos*, and all *Plantae* taxa thereof, including, life, domain, kingdom, phylum, class, order, family, genus, species, super-species, sub-species, varieties, hybrids and chemotypes, phenotypes and genotypes, whether naturally occurring or genetically modified. Preferred plant sources of beta-caryophyllene include at least about 20% beta-caryophyllene, such as, at least about 25%, 30%, 35%, 40%, 45% or 50% beta-caryophyllene.

Functionally equivalent derivatives, analogues or salts of beta-caryophyllene, which are pharmaceutically acceptable, may replace beta-caryophyllene in the present composition. The term "functionally equivalent" as used with respect to derivatives, analogues and salts of beta-caryophyllene, refers to compounds which possess the activity or function of beta-caryophyllene, at least in part, to treat pain and/or inflammation. The term "pharmaceutically acceptable" refers to derivatives, analogues and salts which are physiologically acceptable for use in mammals, and which are not unduly toxic or otherwise unacceptable for such use. The term "mammals" includes human and non-human mammals, including domestic animals, e.g. cats, dogs, rodents, cattle, horses and the like, as well as non-domesticated animals.

Functionally equivalent derivatives or analogues, including structural and functional analogues, of beta-caryophyllene include compounds derived from beta-caryophyllene or a precursor thereof, including isomers thereof. Examples of functionally equivalent derivatives or analogues include, but are not limited to, alpha-humulene, 9-epi-(E)-Caryophyllene, [-]-Caryophyllene oxide or (−)-Epoxycaryophyllene, (1R,4R,6S,10R)-9-Methylene-4,12,12-trimethyl-5-oxatricyclo[8.2.0.0]Caryophyllene, 9-epi-Caryophyllene or (E)-Caryophyllene, epi-, cis-Caryophyllene, (+)(E)-Caryophyllene or 2-epi-(E)-β-Caryophyllene, and Isocaryophyllene (or (Z)-Caryophyllene or β-cis-Caryophyllene or (Z)-Caryophyllene or Bicyclo(7.2.0)undec-4-ene, 4,1 1,1 l-trimethyl-8-methylene-, (1R,4Z,9S)- or cis-Caryophyllene or y-Caryophyllene or [1R-(1R*,4Z,9S*)]-4,1 1,1 l-trimethyl-8-methylenebicyclo[7.2.0]undec-4-ene).

Functionally equivalent salts which are pharmaceutically acceptable salts of beta-caryophyllene are also encompassed herein for use to treat pain and/or inflammation. The term "salts" refers to salts or esters of beta-caryophyllene that retain the desired biological activity of the parent compound to treat pain and/or inflammation, at least in part. Examples of such salts include acid addition salts and base addition salts. Acid addition salts include those derived from non-toxic inorganic acids, such as hydrochloric, nitric, phosphoric, sulfuric, hydrobromic, hydroiodic, phosphorous and the like, as well as from nontoxic organic acids such as aliphatic mono- and dicarboxylic acids, phenyl-substituted alkanoic acids, hydroxy alkanoic acids, aromatic acids, aliphatic and aromatic sulfonic acids and the like. Base addition salts include those derived from alkaline earth metals, such as sodium, potassium, magnesium, calcium and the like, as well as from nontoxic organic amines, such as N,N'-dibenzylethylenediamine, N-methylglucamine, chloroprocaine, choline, diethanolamine, ethylenediamine, procaine and the like.

Although various natural sources of beta-caryophyllene exist which may be incorporated into the present composition, it will be appreciated that beta-caryophyllene for use in the present composition may also be synthetically derived.

The present composition comprises a mixture of beta-caryophyllene, phospholipids and triglycerides.

The present composition may also be combined with one or more pharmaceutically acceptable adjuvants. The expression "pharmaceutically acceptable" means physiologically acceptable for use in the pharmaceutical and veterinary arts, i.e. not being unacceptably toxic or otherwise unsuitable. Examples of pharmaceutically acceptable adjuvants for inclusion in the present composition include those that are suitable for combination with the essential oil active ingredients. Reference may be made to "Remington's: The Science and Practice of Pharmacy", 21st Ed., Lippincott Williams & Wilkins, 2005, for guidance on drug formulations generally. The selection of adjuvant depends on the desired effects following topical administration. Adjuvants for a topical or transdermal composition include compounds that may facilitate delivery of plant-derived essential oils, oleoresins, solutes, distillates, extracts, fermentations, infusions and leaching such as meadowfoam seed oil (*Limnanthes alba*), sweet almond (*Amygdalus communis* var. *dulcis*), arnica (*Arnica montana*), argan (*Argania spinosa* Skeels), avocado (*Persea grattissima*), borage (*Borrago officinalis*), calendula (*Calendula officinalis*), tamanu (*Calophyllum inophyllum*), carrot (*Daucus carota*), wheat germ (*Triticum vulgare*), cocoa butter (*Theobroma cacao*), Shea butter (*Vitellaria paradoxa*), lecithin, cottonseed oil (*Gossypium barbadense*), evening primrose (*Oenothera biennis, O. glazioviana, O. lamardiana, O. riparia*), grapeseed oil (*Vitis vinifera*), hemp (*Cannabis sativa*), jojoba (*Simmondsia sinensis*), macadamia (*Macadamia tetraphylla*), St. John's wort (*Hypericum perforatum*), apricot (*Prunus armeniaca*), hazel (*Corylus avellana*), olive (*Olea europea*), rosehip (*Rosa* spp.), sunflower (*Helianthus annuus*), sesame (*Sesamum indicum*), Carthamus tinctorius and wheatgerm (*Triticum vulgare, Triticum durum, Triticum aestivum*) and all *Plantae taxa* thereof including life, domain, kingdom, phylum, class, order, family, genus, species, genetically modified superspecies, subspecies, varieties, hybrids and chemotypes, phenotypes and genotypes thereof. Other exemplary adjuvants include skin conditioning agents, stabilizers, anti-oxidants, anti-microbial agents, preservatives, colouring agents, fragrance, fixatives, solvent and surface active agents.

In one embodiment, the present composition comprises, Shea Butter (*Vitellaria paradoxa*), white bees wax, beta-caryophylene, ethanol, water, tea tree oil, lecithin, polyethylene glycol, apricot kernel oil and lemon grass oil. Amounts of each may be within the following ranges in the formulation: Shea butter about 40-60%, lecithin about 1-4%, and beta-caryophylene about 6-10%. These active ingredients may optionally be combined water at about 10-20%, ethyl alcohol at 10-20%, white bees wax at about 0.1 to 0.5%, tea tree oil at about 0.025 to 0.2%, lemon grass oil at about 0.025 to 0.2%, apricot kernel oil about 0.5 to 2% and polyethylene glycol at about 1.0 to 3.0%.

A method of treating pain and/or inflammation in a mammal is provided in another aspect of the invention. The method comprises administering a composition comprising a therapeutically effective amount of beta-caryophyllene in combination with phospholipids and triglicerides. The terms "treat", "treating" and "treatment" are used broadly herein to denote methods that moderate, ameliorate, reverse the progression of, reduce the severity of, or prevent pain and/or inflammation. In this regard it is noted that because a wide range of inter-individual variability exists in the perception of pain, the perceived result of the present treatment may vary from mammal to mammal.

The term "pain" is used broadly herein to refer to any neural or non-neural pain including, for example, cancer pain, multiple sclerosis pain, HIV pain, diabetic pain, chemotherapeutic pain, ischemic pain, arthritic pain and pain from inflammation. Neural or neuropathic pain refers to pain resulting from an injury to or malfunction in the peripheral or central nervous system. Neural pain may be triggered by an injury but does not necessarily involve actual damage to the nervous system. Neuropathic pain is frequently chronic. Examples of neuropathic pain include, but are not limited to, lower back pain, repetitive strain injury, migraine and headache, and pain resulting from a disease state such as any type of cancer and/or from other substances to treat said disease state such as chemotherapeutic substances doxorubicin, cisplatin, paclitaxel and any neuroinflammatory pain, disease associated with the immune system, multiple sclerosis, arthritis, trigeminal neuralgia, peripheral neuropathy, complex regional pain syndrome (CRPS), fibromyalgia, TMJ (temporal mandibular joint) pain and inflammatory myopathy. Non-neural or nociceptive pain refers to pain from tissue injury, including for example, sprains, bone breaks or fractures, burns, bumps, bruises, inflammation, obstructions and myofascial pain.

The term "inflammation" refers to a complex biological response of vascular tissues to harmful stimuli, such as pathogens, damaged cells, or irritants. Signs of inflammation include pain, redness, swelling and/or loss of function. Types of inflammation include, but are not limited to, localized inflammation, systemic inflammation, neuroinflammation, bursitis, cystitis, dermatitis, phlebitis, tendonitis, and vasculitis.

The present method includes administration of the composition using any suitable administrable form, formulated accordingly, including one or more appropriate carriers and/or adjuvants. Suitable administrable forms include topical and transdermal.

In one embodiment, the method includes topical application of the composition to a mammal in need of pain and/or inflammation treatment. The composition may be applied to an affected area on the skin of the mammal, or to a site appropriate to target an affected area, e.g. an affected internal area such as the sciatic nerve, joints, muscle, etc. The composition is preferably rubbed into the skin to promote absorption of the active ingredients. The composition is administered at a dosage suitable to treat pain and/or inflammation. In one embodiment, the dosage administered is generally in the range of between about 0.5 to 1.0 ml of a composition comprising from about 50.0 mg/ml to 150 mg/ml beta-caryophylene. As one of skill in the art will appreciate, the dosage may be adjusted upwards or downwards to address the severity of the pain and/or inflammation, or the size of an affected area. The composition is generally applied as needed for a period of time sufficient to treat pain and/or inflammation. For more severe cases, however, the composition may be applied more frequently, e.g. four or more times a day for a period of time sufficient to treat the pain and/or inflammation.

While not wishing to be limited to a particular mode of action, it is believed that the activity of the present composition is specific to the cannabinoid-2 receptor (CB2 receptor), and thus, functions as a CB2 agonist, selectively targeting the CB2 receptor, while not interacting with the psychoactive cannabinoid 1-receptor (CBI receptor). This selectivity of the present composition renders it very effective to treat pain and/or inflammation with minimal side effects. Moreover, the combination of components unexpectedly result in a high degree of pain relief and inflammation reduction presumably through greater absorption and of active ingredients.

In addition to alleviating pain and/or inflammation, the present composition may also provide, or be adapted to provide, one or more of anti-aging, reduced susceptibility to contact from pathogens and insects, neuroprotective, chemoprotective, anti-neuroinflammatory or anti-nociceptive properties. In this regard, it is noted that components of the present composition, namely essential oils that comprise beta-caryophyllene, and minor essential oils present in the preferred embodiment may exhibit one or more of such properties. Additional components may also be added to the present composition to impart one or more of such properties or augment efficacy of any or all properties through additive or synergistic action.

Embodiments of the present invention are described in the following specific examples which are not to be construed as limiting.

Example 1: Formula for Hand and Body Cream

A formulation was prepared with components including shea butter, white bees wax, beta-caryophylene, EtOH, H2O, tea tree oil, lecithin, polyethylene glycol (PEG), apricot kernel oil, lemon grass oil in the amounts shown in Table 1.

TABLE 1

| Formulation for hand body cream | |
|---|---|
| shea butter | 600 gm |
| white bees wax | 2 gm |
| beta-caryophylene | 75 ml |
| EtOH | 150 ml |
| H2O | 150 ml |
| tea tree oil | 500 ul |
| lecithin | 20 gm |
| PEG | 20 ml |
| apricot kernel oil | 10 ml |
| lemon grass oil | 500 ul |

The components were combined to form a homogeneous mixture ready for use.

Example 2: Face Cream

A formulation was prepared using components including shea butter, white bees wax, beta-caryophylene, EtOH, H$_2$O. tea tree oil, lecithin, polyethylene glycol (PEG), apricot kernel oil, lemon grass oil, and Plantasens® Olive Active HP (Unsaponifiable fraction of Olive Oil) in the amounts shown in Table 2.

TABLE 2

| Formulation for hand body cream | |
|---|---|
| shea butter | 600 gm |
| white bees wax | 2 gm |
| beta-caryophylene | 75 ml |
| EtOH | 150 ml |
| H$_2$O | 150 ml |
| tea tree oil | 0.5 ml |
| lecithin | 20 gm |
| PEG | 20 ml |
| apricot kernel oil | 10 ml |
| lemon grass oil | 0.5 ml |
| Plantasens ® Olive Active HP (Unsaponifiable fraction of Olive Oil) | 3.0 ml |

The components were combined to form a homogeneous mixture ready for use.

I claim:
1. A pharmaceutical composition, comprising:
   a) an effective amount of beta-caryophyllene and one or more adjuvants,
   b) wherein the effective amount of beta-caryophyllene is in a range from about 50.0 mg/ml to about 150 mg/ml, and
   c) wherein the one or more adjuvants comprise:
      i) 600 grams shea butter,
      ii) 2 grams white bees wax, iii) 150 ml EtOH,
iv) 150 ml H$_2$O,
v) 0.5 ml tea tree oil,
vi) 20 grams Lecithin,
vii) 20 ml PEG,
viii) 10 ml apricot kernel oil, and
ix) 0.5 ml lemon grass oil.

2. The composition of claim 1, further comprising 3 ml of Unsaponifiable fraction of Olive Oil.

3. A method of treating pain or inflammation of the skin of a mammal comprising topically administering to the skin of the mammal the composition of claim 1.

4. The method of claim 3, wherein the mammal is a human.

* * * * *